US011065035B2

(12) United States Patent
Silver et al.

(10) Patent No.: US 11,065,035 B2
(45) Date of Patent: Jul. 20, 2021

(54) MULTI-MODAL SURGICAL GAS CIRCULATION SYSTEM FOR CONTROLLING A NETWORK OF GAS SEALED ACCESS DEVICES

(71) Applicant: Conmed Corporation, Utica, NY (US)

(72) Inventors: Mikiya Silver, New Haven, CT (US); Michael J. Kane, Clinton, CT (US); Michael J. Augelli, Prospect, CT (US)

(73) Assignee: Conmed Corporation, Utica, NY (US)

( * ) Notice: Subject to any disclaimer, the term of this patent is extended or adjusted under 35 U.S.C. 154(b) by 258 days.

(21) Appl. No.: 16/220,704

(22) Filed: Dec. 14, 2018

(65) Prior Publication Data

US 2020/0187984 A1 Jun. 18, 2020

(51) Int. Cl.
*A61B 17/34* (2006.01)
*A61B 17/00* (2006.01)
*B01D 46/00* (2006.01)
*A61M 13/00* (2006.01)

(52) U.S. Cl.
CPC ...... *A61B 17/3474* (2013.01); *A61B 17/3423* (2013.01); *A61B 17/3498* (2013.01); *A61B 2017/00221* (2013.01); *A61B 2017/00225* (2013.01); *A61B 2017/3419* (2013.01); *A61B 2218/006* (2013.01); *A61M 13/006* (2014.02); *A61M 2205/70* (2013.01); *B01D 46/0005* (2013.01)

(58) Field of Classification Search
CPC ............ A61B 17/3474; A61B 17/3423; A61B 17/3421; A61B 17/3462; A61M 13/003; A61M 13/006
See application file for complete search history.

(56) References Cited

U.S. PATENT DOCUMENTS

| 8,715,219 B2* | 5/2014 | Stearns .............. A61B 17/3474 604/26 |
| 8,795,223 B2 | 8/2014 | Stearns et al. |
| 9,067,030 B2 | 6/2015 | Stearns et al. |
| 9,358,074 B2 | 6/2016 | Schena et al. |
| 9,375,539 B2* | 6/2016 | Stearns .............. A61B 17/3474 |
| 9,526,849 B2 | 12/2016 | Stearns et al. |

(Continued)

OTHER PUBLICATIONS

PCT International Search Report and Written Opinion dated Feb. 7, 2020, issued during the prosecution of PCT International Patent Application No. PCT/US2019/057629.

*Primary Examiner* — Laura A Bouchelle
(74) *Attorney, Agent, or Firm* — Locke Lord LLP; Scott D. Wofsy

(57) ABSTRACT

A system for performing an endoscopic surgical procedure in a surgical cavity is disclosed which includes a primary gas circulation device housing a central processor and a primary pump, the primary pump controlled by the central processor and configured to deliver a flow of pressurized gas to a primary gas delivery lumen and to receive gas from a primary gas return lumen, and a plurality of subordinate gas circulation devices each housing a respective subordinate pump configured to deliver a flow of pressurized gas to a respective subordinate gas delivery lumen and to receive gas from a respective subordinate gas return lumen, wherein the subordinate pump in each subordinate gas circulation device is in networked communication with and controlled by the central processor of the primary gas circulation device.

25 Claims, 14 Drawing Sheets

(56) References Cited

U.S. PATENT DOCUMENTS

| | | |
|---|---|---|
| 9,526,886 B2 | 12/2016 | Mastri et al. |
| 9,907,569 B2 | 3/2018 | Stearns et al. |
| 2005/0137529 A1 | 6/2005 | Mantell |
| 2007/0088275 A1* | 4/2007 | Stearns .............. A61B 17/3423 604/164.01 |
| 2008/0243050 A1* | 10/2008 | Power .................. A61M 13/00 604/26 |
| 2017/0000959 A1* | 1/2017 | Mantell ............... A61M 13/003 |
| 2017/0361084 A1 | 12/2017 | Zergiebel et al. |
| 2018/0133416 A1 | 5/2018 | Silver et al. |
| 2018/0221597 A1 | 8/2018 | Silver |
| 2018/0236186 A1 | 8/2018 | Stearns et al. |
| 2018/0256204 A1 | 9/2018 | Silver et al. |
| 2018/0256205 A1 | 9/2018 | Silver et al. |
| 2018/0256207 A1 | 9/2018 | Augelli et al. |
| 2018/0296245 A1 | 10/2018 | Stearns et al. |
| 2019/0091421 A1* | 3/2019 | Geisz ................. A61M 13/003 |

* cited by examiner

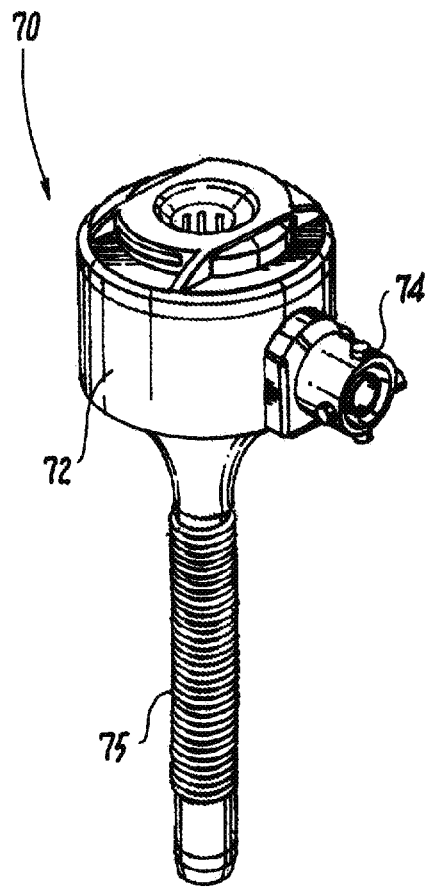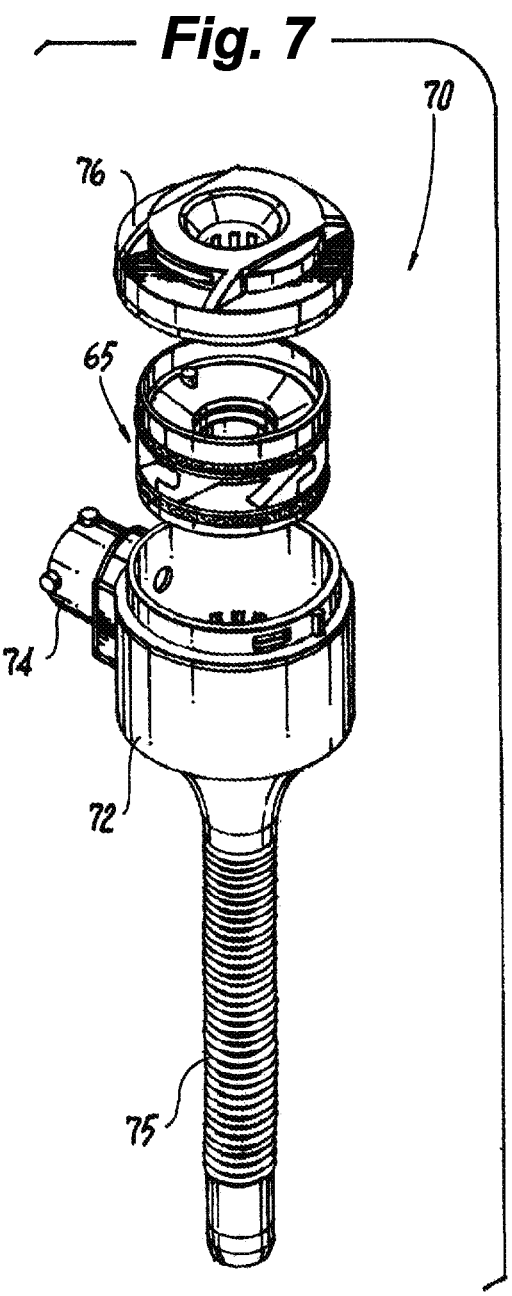
Fig. 6
Fig. 7

MULTI-MODAL SURGICAL GAS CIRCULATION SYSTEM FOR CONTROLLING A NETWORK OF GAS SEALED ACCESS DEVICES

BACKGROUND OF THE INVENTION

1. Field of the Invention

The subject invention is directed to endoscopic surgery, and more particularly, to a multi-modal surgical gas circulation system that is adapted and configured to control and operate a network of gas sealed access ports used during an endoscopic surgical procedure.

2. Description of Related Art

Endoscopic surgical techniques are well known. Indeed, laparoscopic surgical procedures performed in the abdominal cavity, such as such as cholecystectomies, appendectomies, hernia repair and nephrectomies have become commonplace. Benefits of such minimally invasive surgical procedures include reduced trauma to the patient, reduced opportunity for infection, and decreased recovery time. Such procedures are typically performed through a device known as a trocar or cannula, which facilitates the introduction of laparoscopic instruments into the abdominal cavity of a patient.

Endoscopic surgical procedures performed in other surgical cavities or areas of the body include thoracoscopic surgical procedures performed in the thoracic cavity of a patient, as well as, endo-luminal surgical procedures, such as trans-anal and trans-esophageal surgical procedures.

Endoscopic surgical procedures commonly involve filling or "insufflating" the surgical cavity with a pressurized fluid, such as carbon dioxide, to create an operating space. In the case of laparoscopy in the abdominal cavity, this is referred to as a pneumoperitoneum. Insufflation can be carried out by a surgical access device, such as a trocar, equipped to deliver insufflation fluid, or by a separate insufflation device, such as an insufflation (veress) needle.

The trocar must also provide a way to maintain the pressure within the surgical cavity by sealing between the trocar and the surgical instrument being used, while still allowing at least a minimum amount of freedom of movement for the surgical instruments. Mechanical seals are typically provided on trocars to prevent the escape of insufflation gas from the surgical cavity. These seals often comprise a duckbill-type valve made of a relatively pliable material, which seals around an outer surface of a surgical instrument passing through the trocar.

SurgiQuest, Inc., a wholly owned subsidiary of ConMed Corporation has developed unique gas sealed surgical access devices that permit ready access to an insufflated surgical cavity without the need for conventional mechanical seals, as described, for example, in U.S. Pat. Nos. 8,795,223 and 9,907,569, the disclosures of which are herein incorporated by reference in their entireties. These gas sealed access devices have an inner tubular body portion that defines a central lumen for introducing surgical instruments to the surgical cavity and an outer tubular body portion that defines an annular outer lumen surrounding the inner tubular body portion for delivering insufflation gas to the surgical cavity and for facilitating periodic sensing of cavity pressure. During use, pressurized gas is delivered to the access device, where it is accelerated by internal jet nozzles to create a gaseous sealing zone within the central lumen of the access device. Gas that has been used to generate the gaseous sealing zone is carried away from the access device by way of a suction line.

These dual-lumen gas sealed access devices are designed for use with a unique multi-modal surgical gas delivery device, as described in commonly assigned U.S. Pat. Nos. 9,067,030 and 9,526,849, the disclosures of which are herein incorporated by reference. This gas delivery device includes an insufflation subunit for delivering insufflation gas to the outer annular lumen of the access device, and for taking periodic pressure readings from the surgical cavity. The gas delivery device further incudes a gas circulation pump for delivering pressurized gas to the nozzle jets located within in the access device and for carrying away spent gas from the access device, thereby forming a gas recirculation path between the pump and the access port.

While these early multi-modal surgical gas delivery devices are extremely versatile, they are limited in that the gas circulation pump included therein is designed to provide enough output power to effectively generate a gaseous seal within a single gas sealed access port, and in certain limited instances two gas sealed access ports. This limits the types of surgical procedures that can be effectively performed using gas sealed access ports.

It would be beneficial therefore to provide a multi-modal surgical gas delivery system that is capable of providing a sufficient amount of output power to generate gaseous seals in a plurality of gas sealed access ports. This would be extremely useful in the performance of robotically assisted laparoscopic surgical procedures in which the use of multiple gas sealed trocars is preferable in order to reduce gas leakage, instrument drag and mechanical wear and tear caused by access ports that have mechanical seals. The subject invention provides a solution.

SUMMARY OF THE DISCLOSURE

The subject invention is directed to a new and useful multi-modal surgical gas circulation system for performing an endoscopic surgical procedure in a surgical cavity, which overcomes certain disadvantages associated with prior art multi-modal surgical gas delivery systems. It includes a primary gas circulation device housing a primary pump configured to deliver a flow of pressurized gas to a primary gas delivery lumen and to receive gas from a primary gas return lumen, and primary gas sealed access port configured to receive pressurized gas from the primary gas delivery lumen to generate a gaseous seal therein and to return gas used to generate the gaseous seal back to the primary pump through the primary gas return lumen, so as to maintain a stable pressure level within the surgical cavity.

The primary gas circulation device further houses an insufflator for delivering insufflation gas to the surgical cavity through an insufflation lumen and periodically measuring pressure within the surgical cavity through the insufflation lumen.

The system further includes at least one subordinate gas circulation device in communication with and controlled by the primary gas circulation device and housing a subordinate pump configured to deliver a flow of pressurized gas to a subordinate gas delivery lumen and to receive gas from a subordinate gas return lumen, and at least one subordinate gas sealed access port configured to receive pressurized gas from the subordinate gas delivery lumen to generate a gaseous seal therein and to return gas used to generate the gaseous seal back to the subordinate pump through a subordinate gas return lumen.

In accordance with one embodiment of the subject invention, the primary gas sealed access port is a dual lumen gas sealed access port that includes coaxially arranged inner and outer tubular body portions defining an annular insufflation passage therebetween for receiving insufflation gas from the insufflator through the insufflation lumen. An example of a dual lumen gas sealed access port is disclosed in commonly assigned U.S. Pat. No. 8,795,223, which was previously incorporated herein by reference.

In accordance with another embodiment of the subject invention, an insufflation sleeve is provided for receiving insufflation gas from the insufflator through the insufflation lumen. In such an embodiment, the primary gas sealed access port is a single lumen gas sealed access port that includes a single tubular body portion coaxially arranged within the insufflation sleeve. Examples of a single lumen gas sealed access port are disclosed in commonly assigned U.S. Patent Application Publication No. 2018/0256205, which is incorporated herein by reference in its entirety.

In an embodiment of the invention, the single lumen gas sealed access port has a separable two-part housing including a lower housing portion connected to the single tubular body portion and an upper housing portion releasably attached to the lower body portion. The lower housing portion includes structure to facilitate manipulation by a robotic surgical system during a robotically assisted endoscopic surgical procedure. An example of a single lumen gas sealed access port having a separable two-part housing for use in robotically assisted endoscopic surgical procedures is disclosed in commonly assigned U.S. Patent Application Publication No. 2018/0256207, which is incorporated herein by reference in its entirety.

In another embodiment of the invention, a valve sealed access device may be provided for receiving insufflation gas from the insufflator through the insufflation lumen. Alternatively, an insufflation needle may be provided for receiving insufflation gas from the insufflator through the insufflation lumen.

The system further includes a primary filter cartridge configured for reception in the primary gas circulation device to communicate with the primary gas delivery lumen and the primary gas return lumen. Alternatively, the system includes a primary filter cartridge configured for reception in the primary gas circulation device to communicate with the primary gas delivery lumen, the primary gas return lumen and an insufflation lumen. In either embodiment, the at least one subordinate gas circulation device includes a subordinate filter cartridge communicating with the subordinate gas delivery lumen and the subordinate gas return lumen.

In accordance with a preferred embodiment of the subject invention, the primary gas circulation device houses a central processor for controlling the primary pump of the primary gas circulation device and the subordinate pump of the at least one subordinate gas circulation device. It is envisioned that the at least one subordinate gas circulation device would be in wireless communication or in wired communication with the central controller of the primary gas circulation device.

It is also envisioned that the central processor would be adapted and configured to conduct a multi-staged calibration process for calibrating a pneumatic performance range of the primary gas sealed access port and the at least one subordinate gas sealed access port. In a preferred embodiment of the subject invention, each gas sealed access port would be calibrated one by one, and then the pump in each subordinate gas circulation device would maintain that required amount of pneumatic power supply without varying it. Only the primary pump in the primary gas circulation device would vary its pneumatic supply in order to compensate for over pressure and under pressure conditions arising in the system.

It is envisioned that the primary gas circulation device includes a data reader for detecting a machine readable data signature of the primary filter cartridge to determine a physical characteristic thereof, and the at least one subordinate gas circulation device includes a data reader for detecting a machine readable data signature of the subordinate filter cartridge to determine a physical characteristic thereof. In use, the data reader in each subordinate device would communicate with the central processor in the primary device to determine how many and/or what specific tube sets are connected for use. This would drive the calibration algorithm for effectively running the system.

A related system designed to launch a usage mode in a multimodal gas circulation device is disclosed in commonly assigned U.S. Patent Application Publication No. 2018/0221597, which is incorporated herein by reference in its entirety. As described therein, the machine readable data signature of the subject invention could be a radio frequency identification (RFID) reader, a bar code reader or a near field communication device.

In an embodiment of the invention, the subordinate pump of the at least one subordinate gas circulation device is driven by AC power. Alternatively, the subordinate pump of the at least subordinate gas circulation device is driven by a DC motor.

The subject invention is also directed to a system for performing an endoscopic surgical procedure in a surgical cavity, which includes a primary gas circulation device housing a central processor and a primary pump, the primary pump controlled by the central processor and configured to deliver a flow of pressurized gas to a primary gas delivery lumen and to receive gas from a primary gas return lumen, and a plurality of subordinate gas circulation devices each housing a respective subordinate pump configured to deliver a flow of pressurized gas to a respective subordinate gas delivery lumen and to receive gas from a respective subordinate gas return lumen, wherein the subordinate pump in each subordinate gas circulation device is in networked communication with and controlled by the central processor of the primary gas circulation device.

The primary gas circulation device also houses an insufflator configured to deliver insufflation gas to the surgical cavity through an insufflation lumen and for periodically measuring pressure within the surgical cavity through the insufflation lumen. The system further incudes a primary gas sealed access port configured to receive pressurized gas from the primary gas delivery lumen to generate a gaseous seal therein and to return gas used to generate the gaseous seal back to the primary pump through the primary gas return lumen, so as to maintain a stable pressure level within the surgical cavity. In one instance, the primary gas sealed access port is configured to receive insufflation gas from the insufflation lumen. Alternatively, insufflation gas may be delivered to an insufflation needle or to a conventional valve sealed trocar.

The system further includes a secondary gas sealed access port operatively associated with each subordinate gas circulation device and configured to receive pressurized gas from a respective subordinate gas delivery lumen to generate a gaseous seal therein and to return gas used to generate the gaseous seal back to a respective subordinate pump through a respective subordinate gas return lumen.

The subject invention is also directed to a system for performing an endoscopic surgical procedure in a surgical cavity, which includes a single lumen gas sealed access port having a proximal housing portion containing an annular nozzle assembly for generating a gaseous seal within the proximal housing portion and a tubular body portion depending distally from the proximal housing portion, and an insufflation sleeve for defining a central bore for receiving the tubular body portion of the gas sealed access port so that an insufflation passage is formed between an inner peripheral surface of the insufflation sleeve and an outer peripheral surface of the tubular body portion of the gas sealed access port.

Preferably, the proximal housing portion of the single lumen gas sealed access port is adapted and configured for connection with a with a gas delivery lumen and a gas return lumen communicating with a pump, and the insufflation sleeve is adapted and configured for connection with an insufflation lumen communicating with an insufflator.

These and other features of the gas circulation system of the subject invention will become more readily apparent to those having ordinary skill in the art to which the subject invention appertains from the detailed description of the preferred embodiments taken in conjunction with the following brief description of the drawings.

BRIEF DESCRIPTION OF THE DRAWINGS

So that those skilled in the art will readily understand how to make and use the networked gas circulation system and gas sealed access devices of the subject invention without undue experimentation, preferred embodiments thereof will be described in detail herein below with reference to the figures wherein:

FIG. 6 is an enlarged perspective view of a single lumen gas sealed access port utilized with the system shown in FIGS. 5 and 5A, with the housing portion separated from the tubular body portion;

FIG. 7 is an exploded perspective view of the single lumen gas sealed access port shown in FIG. 6;

DETAILED DESCRIPTION OF THE PREFERRED EMBODIMENTS

Figure 1:
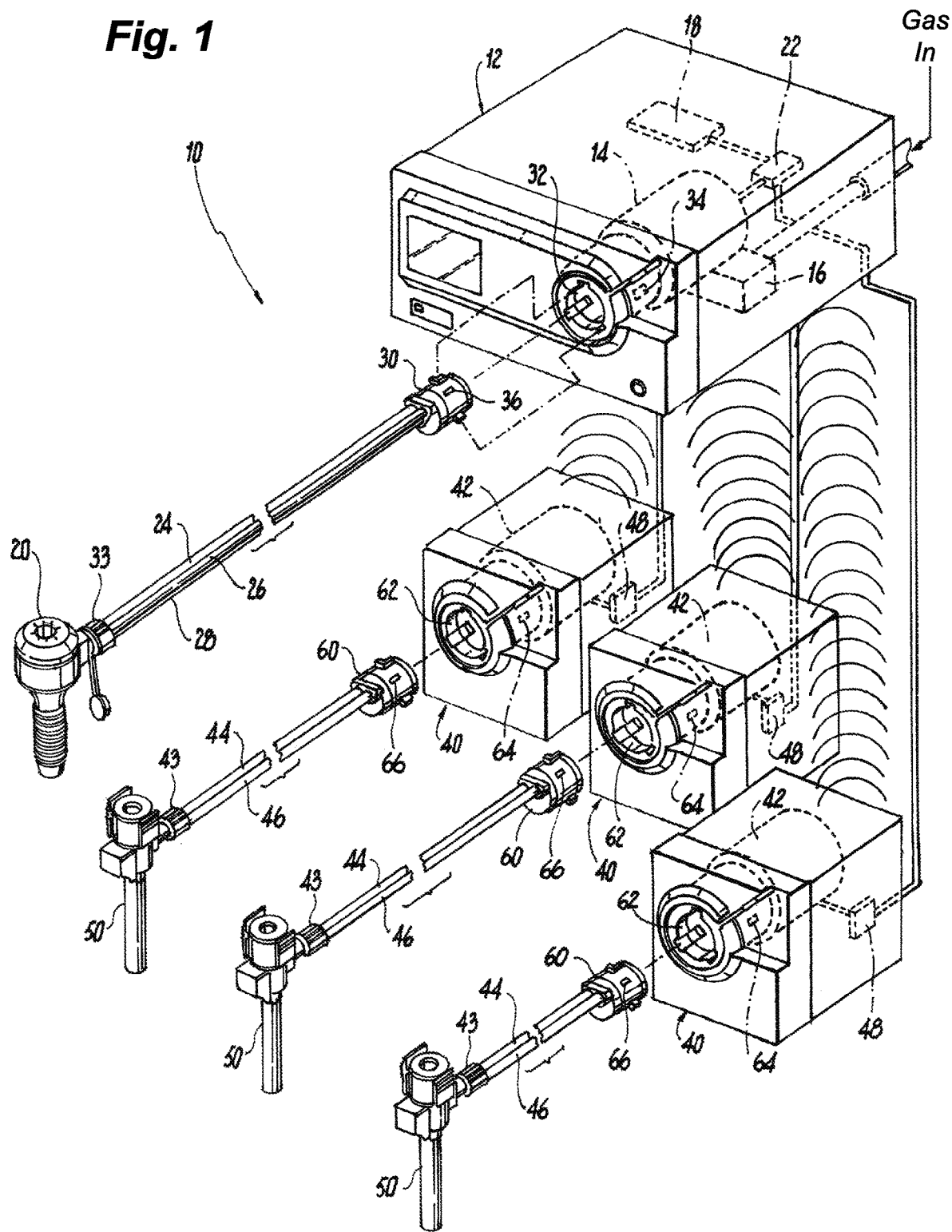
FIG. 1 is a perspective view of an embodiment of the networked gas circulation system of the subject invention, wherein a dual lumen gas sealed access port is associated with the primary gas circulation device and a two-part single lumen gas sealed access port is associated with each secondary gas circulation device in the network.

Referring now to the drawings wherein like reference numerals identify similar structural elements and features of the subject invention, there is illustrated in FIG. 1 a preferred embodiment of a networked multi-modal gas circulation system 10 for performing an endoscopic surgical procedure in a surgical cavity of a patient involving a plurality of gas sealed access devices for introducing surgical instrumentation into the surgical cavity. In particular, the networked multi-modal gas circulation system 10 of the subject invention is designed for use in the performance of a laparoscopic surgical procedure in the abdominal cavity of a patient, which involves a plurality of gas sealed trocars for introducing laparoscopic surgical instrumentation into the abdominal cavity.

Those skilled in the art will readily appreciate that this system is optimally designed for use in performing robotically assisted laparoscopic surgical procedures involving multiple gas sealed trocars or access ports, such as those performed using the da Vinci Xi robotic surgical system that has been developed by Intuitive Surgical of Sunnyvale, Calif., an example of which is disclosed in U.S. Pat. No. 9,358,074, the disclosure of which is incorporated by reference herein.

Referring to FIG. 1, the multi-modal gas circulation system 10 of the subject invention includes a primary gas circulation device 12 housing a primary pump 14, an insufflator 16 and a central processing unit (CPU) 18. The primary gas circulation device 12 also houses a primary pump controller 22 connected to the CPU 18 for controlling the primary gas circulation pump 14.

The primary gas circulation device 12 is a multi-modal gas delivery device of the type disclosed in commonly assigned U.S. Pat. Nos. 9,067,030 and 9,526,849, the disclosures of which are herein incorporated by reference. The primary gas circulation device 12 is adapted and configured to cooperate with a dual lumen gas sealed access port 20 of the type disclosed in commonly assigned U.S. Pat. No. 8,795,223 the disclosure of which are herein incorporated by reference.

Figure 2:
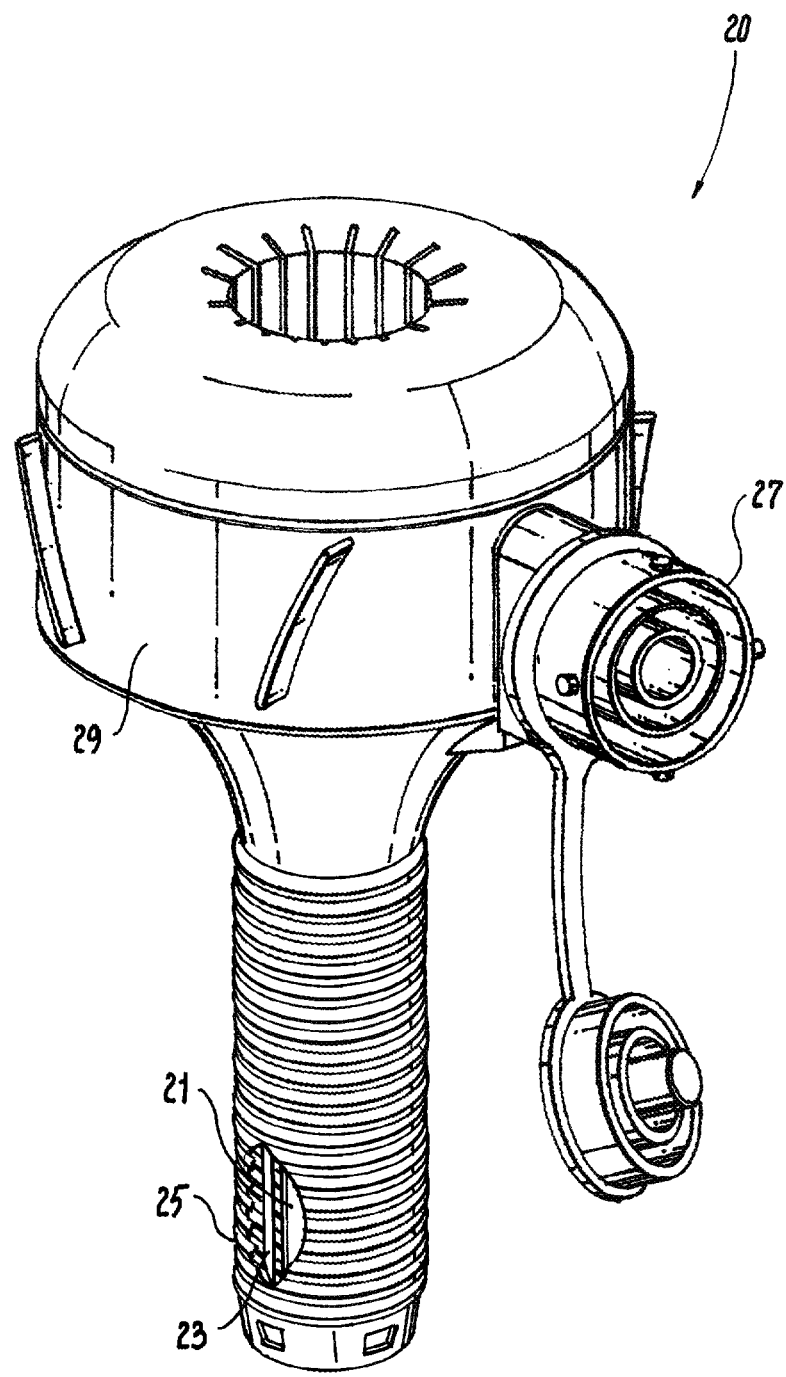
FIG. 2 is an enlarged perspective view of a dual lumen gas sealed access port utilized with the system shown in FIG. 1.

The dual lumen gas seal access port 20 is individually illustrated in FIG. 2 for further clarity. In brief, the dual lumen gas sealed access port 20 includes coaxially arranged inner and outer tubular body portions 21 and 25 defining an annular insufflation passage 23 therebetween and a proximal housing portion 29. The inner tubular body portion 21 is configured to accommodate the passage of surgical instrumentation into the surgical cavity of a patient. The insufflation passage 23 receives insufflation gas from the insufflator 16 and facilitates periodic sensing of cavity pressure. A tri-lumen connector fitting 27 is operatively associated with a proximal housing portion 29 for connecting the access port 20 to a filtered tube set described in further detail below.

The primary pump 14 housed in the primary gas circulation device 12 is configured to deliver a flow of pressurized gas to the gas sealed access port 20 by way of a primary gas delivery lumen 24 to generate a gaseous seal therein and it is further configured to receive "spent" gas that has been used to generate the gaseous seal from the gas sealed access port 20 through a primary gas return lumen 26. The insufflator 16 housed in the primary gas circulation device 12 is configured to receive insufflation gas from an external source (i.e., a portable tank or gas supply line) and deliver it to the gas sealed access port 20 and periodically measure pressure within the surgical cavity through an insufflation lumen 28. The distal ends of the gas delivery lumen 24, gas return lumen 26 and insufflation lumen 28 are connected to the coupling 33, which is designed to couple with the tri-lumen fitting 27 of access port 20, as disclosed for example in commonly assigned U.S. Pat. No. 9,526,886, the disclosure of which is herein incorporated by reference in its entirety.

A primary filter cartridge 30 communicates with the primary gas delivery lumen 24, the primary gas return lumen 26 and the insufflation lumen 28, and it is configured for reception in a front portal 32 of the primary gas circulation device 12. A filter interface such as this is disclosed in commonly assigned U.S. Pat. No. 9,067,030, which is incorporated herein by reference in its entirety.

The primary gas circulation device 12 preferably includes a data reader for detecting or otherwise reading a machine readable data signature within portal 32. For example, the primary gas circulation device 12 preferably includes a radio frequency identification (RFID) reader 34 for detecting an RFID signature of a data element or tag 36 on the primary filter cartridge 30 to determine a physical characteristic of the filer cartridge, for example, the type or number of tubes or lumens associated therewith. Alternatively, the machine readable device could be a bar code reader or a near field communications device. This feature of the system will be discussed in more detail below.

With continuing reference to FIG. 1, the multi-modal gas circulation system 10 further includes at least one and preferably a plurality of subordinate gas circulation devices 40 that are in communication with and controlled by the primary gas circulation device 12. More particularly, each subordinate gas circulation device 40 includes a subordinate pump controller 48 that communicates with the CPU 18 of the gas circulation device 12, as described in more detail below. It is envisioned that each subordinate gas circulation device 40 would be relatively small in size as compared to the primary device 12, and all of these gas circulation devices could be supported for use in a common chassis, rack or cart in a convenient manner.

Each of the subordinate gas circulation devices 40 is adapted and configured to cooperate with a two-part single lumen gas sealed access port 50, of the type disclosed in U.S. Patent Application Publication No. 2018/0256207, which has been previously incorporated by reference, and will be discussed briefly below with reference to FIGS. 3 and 4. Each subordinate gas circulation device 40 houses a subordinate pump 42 configured to deliver a flow of pressurized gas to the two-part single lumen gas sealed access port 50 by way of a subordinate gas delivery lumen 44 to generate a gaseous seal therein and it is further configured to receive "spent" gas that has been used to generate the gaseous seal from the gas sealed access port 50 through a subordinate gas return lumen 46. The distal end of the gas delivery lumen 44 and the distal end of the gas return lumen 46 are operatively associated with a connective coupling 43.

Figure 3:
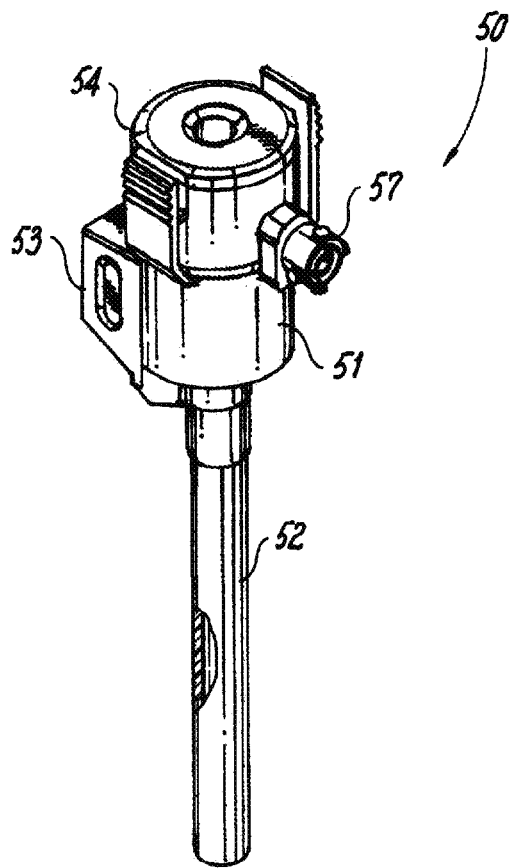
FIG. 3 is an enlarged perspective view of a two-part single lumen gas sealed access port utilized with the system shown in FIG. 1.

As illustrated in FIG. 3, the gas sealed access port 50 has a separable two-part housing including a lower housing portion 51 connected to the single tubular body portion 52 and an upper housing portion 54 releasably attached to the lower body portion 51. The lower housing portion 51 includes flange structure 53 to facilitate manipulation by a robotic surgical system during a robotically assisted endoscopic surgical procedure.

Figure 4:
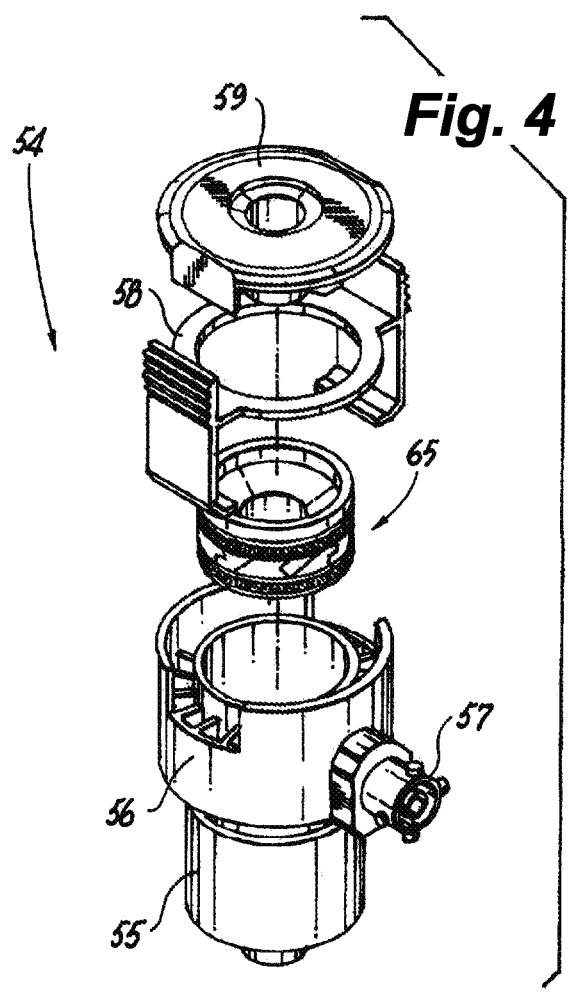
FIG. 4 is an exploded perspective view of the housing portion of the two-part gas sealed access port of FIG. 3.

As shown in FIG. 4, the upper housing portion 54 includes a lower body portion 55 which seats in the lower housing portion 51, an upper body portion 56 that houses an annular nozzle assembly 65 for generating a gaseous seal and a latch assembly for releasably securing the upper housing portion 54 to the lower housing portion 51. The annular nozzle assembly 65 is described in greater detail in commonly assigned U.S. Pat. No. 9,907,569, the disclosure of which is herein incorporated by reference in its entirety. In addition, the lower body portion 56 includes a dual-lumen fitting 57 which is designed to couple with the connector 43. A dual lumen coupling arrangement such as this is illustrated FIGS. 21 through 26 of commonly assigned U.S. Patent Application Publication 2017/0361084, the disclosure of which is herein incorporated by reference.

The subordinate pump 42 is preferably designed to only provide enough output power to generate the gaseous seal in the access port 50, without the need for additional power to compensate for leakage from the surgical cavity. That functionality would be left to the primary pump 14 in the primary gas delivery device 12. Furthermore, the primary gas delivery device 12 would be responsible for smoke evacuation from the surgical cavity and for handling over-pressure conditions in which gas is released through the access port 20 and under-pressure conditions in which air is entrained into the surgical cavity through the access port 20.

A subordinate filter cartridge 60 communicates with the subordinate gas delivery lumen 44 and the subordinate gas return lumen 46 and it is configured for reception in a front portal 62 of each subordinate gas circulation device 40. Each subordinate gas circulation device 40 preferably includes a data reader. For example, each gas circulation device 40 preferably includes an RFID reader 64 for detecting an RFID signature of a data element or tag 66 on an outer surface of the subordinate filter cartridge 60 to determine a physical characteristic of the subordinate filer cartridge 60, such as the characteristics of the set of tubes or lumens associated therewith. It is envisioned that other data transmission means can be employed to convey the physical characteristics of the filter cartridges, such as, for example, bar code readers and near field communication devices. A similar feature is disclosed in commonly assigned U.S. Patent Application Publication 2017/0361084, the disclosure of which is herein incorporated by reference. This feature of the subject system will be discussed in more detail below.

It is further envisioned that each subordinate gas circulation device 40 would include a separate internal fluid detection/sensing system that works in coordination with the subordinate filter cartridge 60, as described in commonly assigned U.S. Pat. No. 9,067,030, the disclosure of which is incorporated herein by reference.

In accordance with a preferred embodiment of the subject invention, the central processor 18 housed within the primary gas delivery device 12 of gas circulation system 10 is adapted and configured to control the primary pump controller 22 of the primary gas delivery device 12 and the subordinate pump controller 48 of each subordinate gas circulation device 40. It is envisioned that the subordinate pump controller 48 of each subordinate gas circulation device 40 would communicate with the primary gas circulation device 12 through the CPU 18 by way of a wireless communication link such as through Bluetooth, NFC or Wi-Fi, or by way of a wired communication link such as through a wired BUS protocol communications such as MOD BUS or CAN BUS serial communication protocols, as illustrated in FIG. 1.

The central processor 18 is also preferably adapted and configured to conduct a multi-staged calibration process for calibrating a pneumatic performance range of the primary gas sealed access port 20 and each of the subordinate gas sealed access ports 50 associated therewith. In a preferred embodiment of the subject invention, each gas sealed access port would be calibrated one by one, and then the pump 42 is each subordinate gas circulation device 40 would maintain that required amount of pneumatic power supply without varying it. Only the primary pump 14 in the primary gas circulation device 12 would vary its pneumatic supply in order to compensate for over pressure and under pressure conditions arising in the system 10.

In use, the RFID reader 64 (or a similar data reader) located in the portal 62 of each subordinate device 40 would read the data carrier 66 on the filter cartridge 60 and communicate back to the CPU 18 in the primary gas circulation device 12 by way of its respective subordinate controller 48 to express how many and/or what type of tubes or lumens are connected to the cartridge 60 received for use within each device 40. This communication would drive a set-up calibration algorithm stored in memory and managed by the CPU 18 that would be used to effectively run the system 10.

It is expected that there would be a process designed to have the user remove obturators within each access port one at a time to calibrate each gaseous seal. First, the obturator in the primary pneumatically sealed access port 20 would be removed by the user. Then, for the next available subordinate pneumatically sealed access port 50, the user would remove an obturator for the second seal and the system would go through the next stage of this multi-stage calibration. During this time, the primary tube set (24, 26, 28) associated with filter cartridge 30 and access port 20 would be responsible for all pressure sensing activity by way of the insufflation lumen 26.

Figure 5:
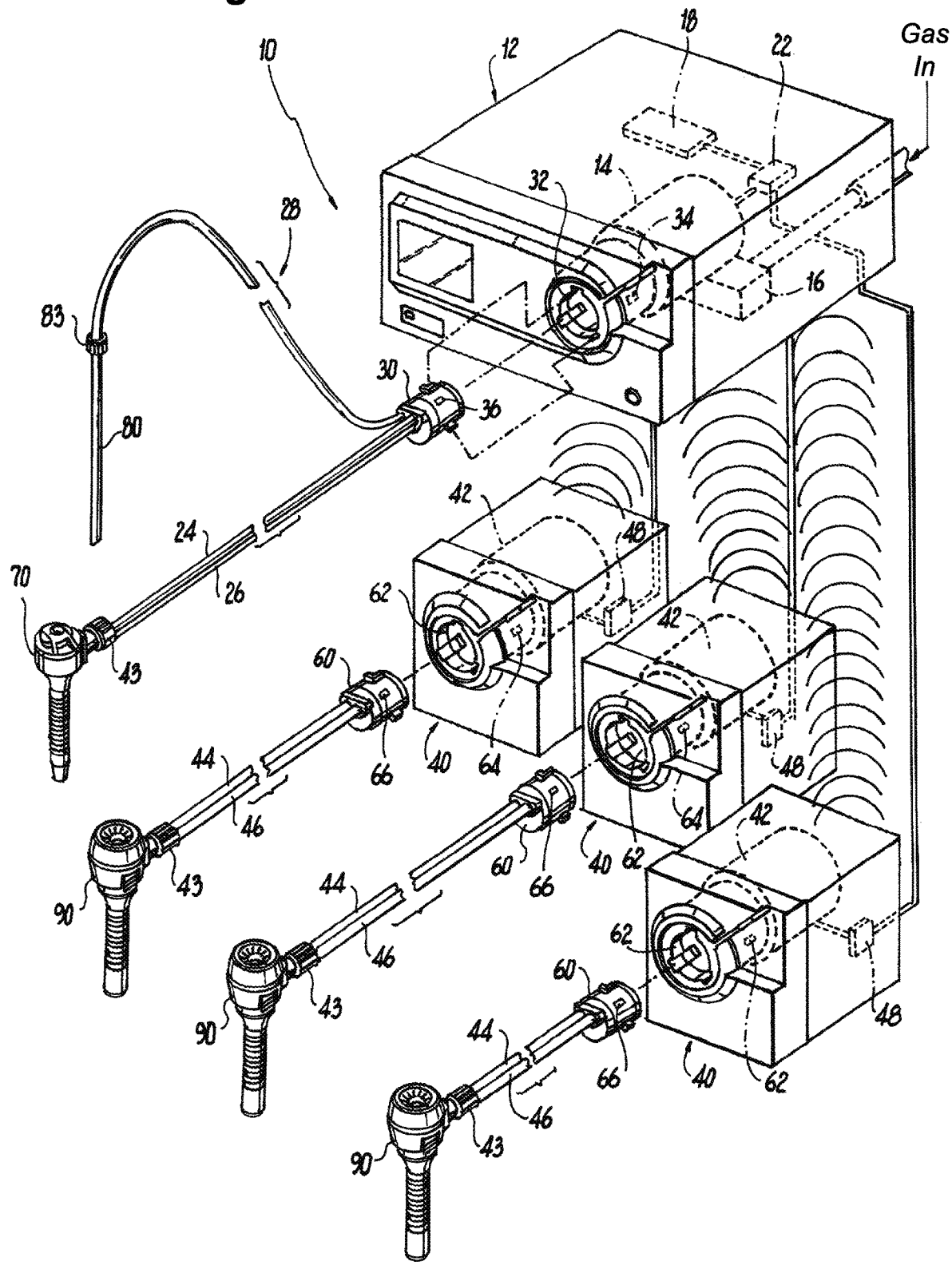
FIG. 5 is a perspective view of another embodiment of the networked gas circulation system of the subject invention, wherein a single lumen gas sealed access port (see FIG. 9) and a veress needle are associated with the primary gas circulation device and a two-part single lumen gas sealed access port is associated with each secondary gas circulation device in the network.

Referring now to FIG. 5, there is illustrated another embodiment of the gas circulation system 10 of the subject invention, which includes a primary gas circulation device 12 and a plurality of networked subordinate gas circulation devices 40, in the same configuration as depicted in FIG. 1 above. In this embodiment however, the access devices differ from those illustrated in FIG. 1. In particular, the primary gas circulation device 12 is in pneumatic communication with a single lumen gas sealed access port 70 and a conventional veress type insufflation needle 80. More particularly, the access port 70 communicates with the gas circulation device 12 by way of a gas delivery lumen 24 and a gas return lumen 26, and the veress needle 80 communicates with the gas circulation device 12 by way of insufflation lumen 28 which has a distal connective coupling 83.

Each of the subordinate gas circulation devices 40 are in pneumatic communication with a two-part single lumen gas sealed access port 90, which is designed for conventional laparoscopic surgery, not robotically assisted laparoscopic surgery. More particularly, each access port 90 communicates with a respective subordinate gas circulation device 40 by way of a gas delivery lumen 44 and a gas return lumen 46.

Figure 5A:
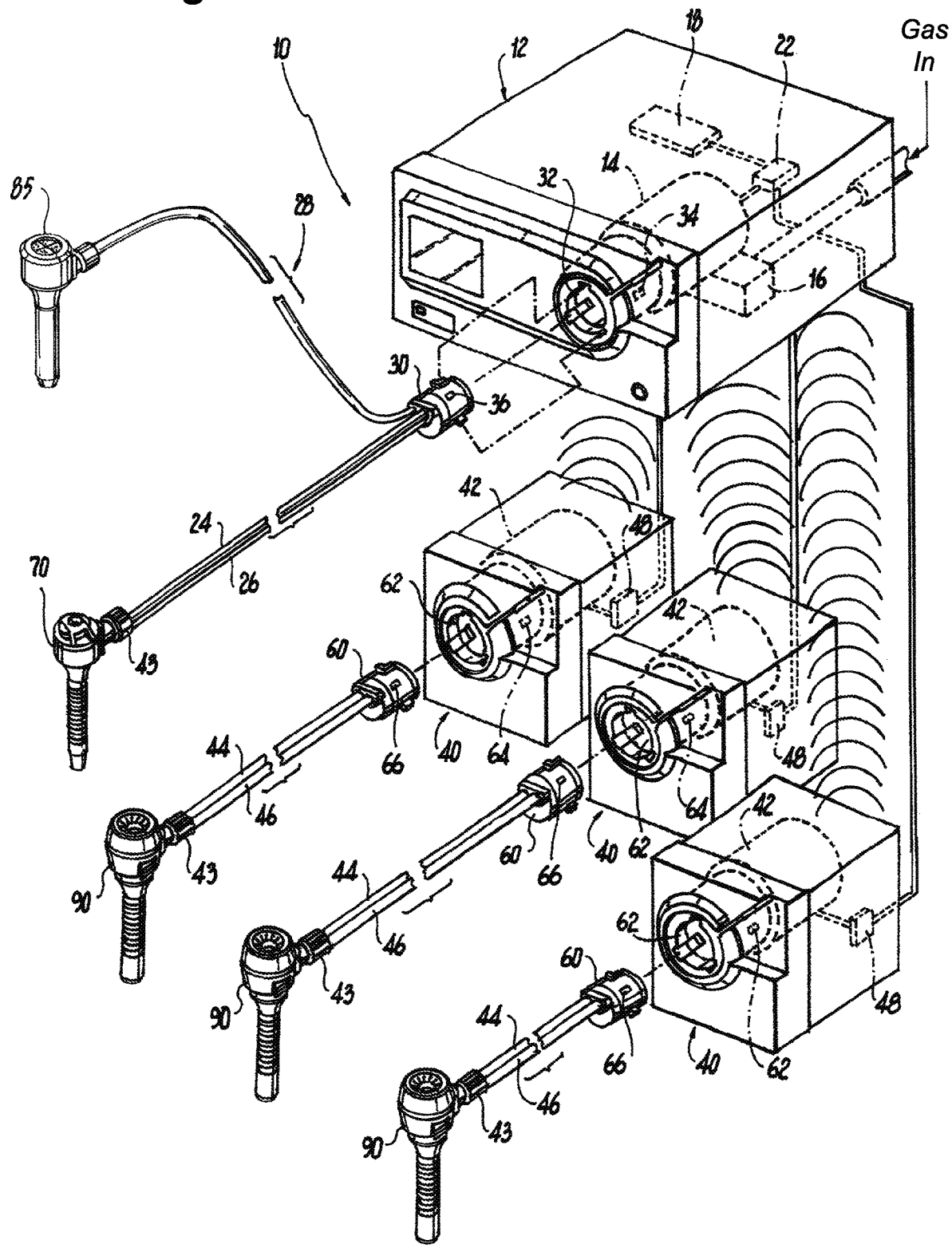
FIG. 5A is a perspective view of the system shown in FIG. 5, wherein a conventional valve sealed access port is associated with the primary gas circulation device, instead of a veress needle.

FIG. 5A illustrates a system similar to the system of FIG. 5, wherein a conventional valve sealed access port 85 is associated with the primary gas circulation device 12 instead of the veress needle 80. More particularly, the valve sealed access port 85 communicates with the gas circulation device 12 by way of insufflation lumen 28. A multi-lumen tube set for use with the system of FIGS. 5 and 5A is disclosed in commonly assigned U.S. Patent Application Publication No. 2018/0256204, the disclosure of which is herein incorporated by reference in its entirety.

The single lumen gas sealed access port 70 is individually illustrated in FIGS. 6 and 7, and is described in greater detail in U.S. Patent Application Publication No. 2018/0256205, which has been previously incorporated herein by reference. The two-part single lumen gas sealed access port 90 is individually illustrated in FIGS. 8 and 9, and is described in greater detail in U.S. Patent Application Publication No. 2018/0256207, which has been previously incorporated herein by reference.

Referring to FIGS. 6 and 7, the single lumen gas sealed access port 70 includes a proximal housing portion 72 with an elongated tubular body portion 75 extending distally therefrom. The proximal housing 72 defines an interior plenum chamber that houses an annular nozzle assembly 65 for generating a gaseous seal and an end cap 76 for enclosing the nozzle assembly 65 within the chamber. The proximal housing 72 further includes a dual-lumen connector 74 for cooperating with the coupling 43 at the distal end of gas delivery lumen 44 and gas return lumen 46, as shown in FIG. 5.

Figure 8:
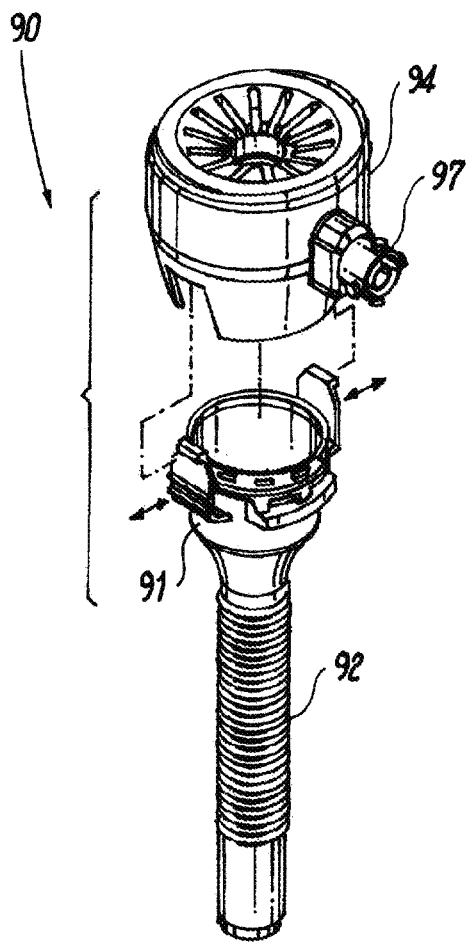
FIG. 8 is an enlarged perspective view of a two-part single lumen gas sealed access port utilized with the system shown in FIGS. 5 and 5A, with the housing portion separated from the tubular body portion.
Figure 9:
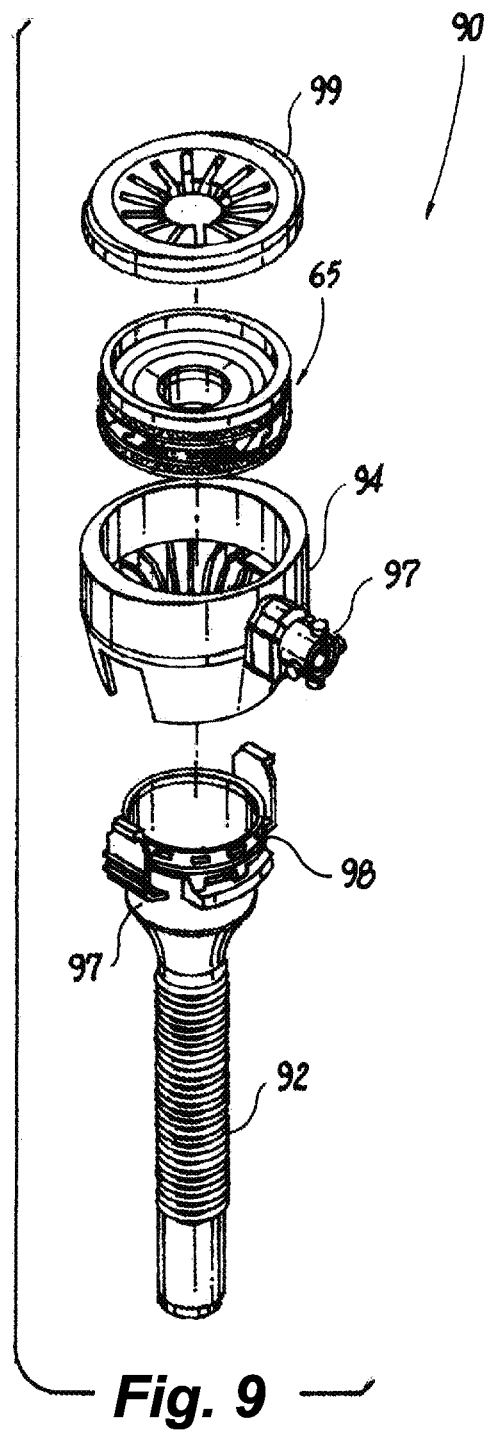
FIG. 9 is an exploded perspective view of the two-part single lumen gas sealed access port shown in FIGS. 5 and 5A.

Referring to FIGS. 8 and 9, the gas sealed access port 90 has a separable two-part housing including a lower housing portion 91 with a single tubular body portion 92 extending therefrom and an upper housing portion 94 releasably attached to the lower housing portion 91 by a latch assembly 98 provided on the lower housing portion 91. The upper housing portion 94 defines a plenum chamber with an end cap 99 that houses an annular nozzle assembly 65 for generating a gaseous seal. In addition, the upper housing portion 94 includes a dual-lumen fitting 97 which is designed to couple with the connector 43 at the distal end of gas delivery lumen 44 and gas return lumen 46, as shown in FIG. 5.

Figure 10:
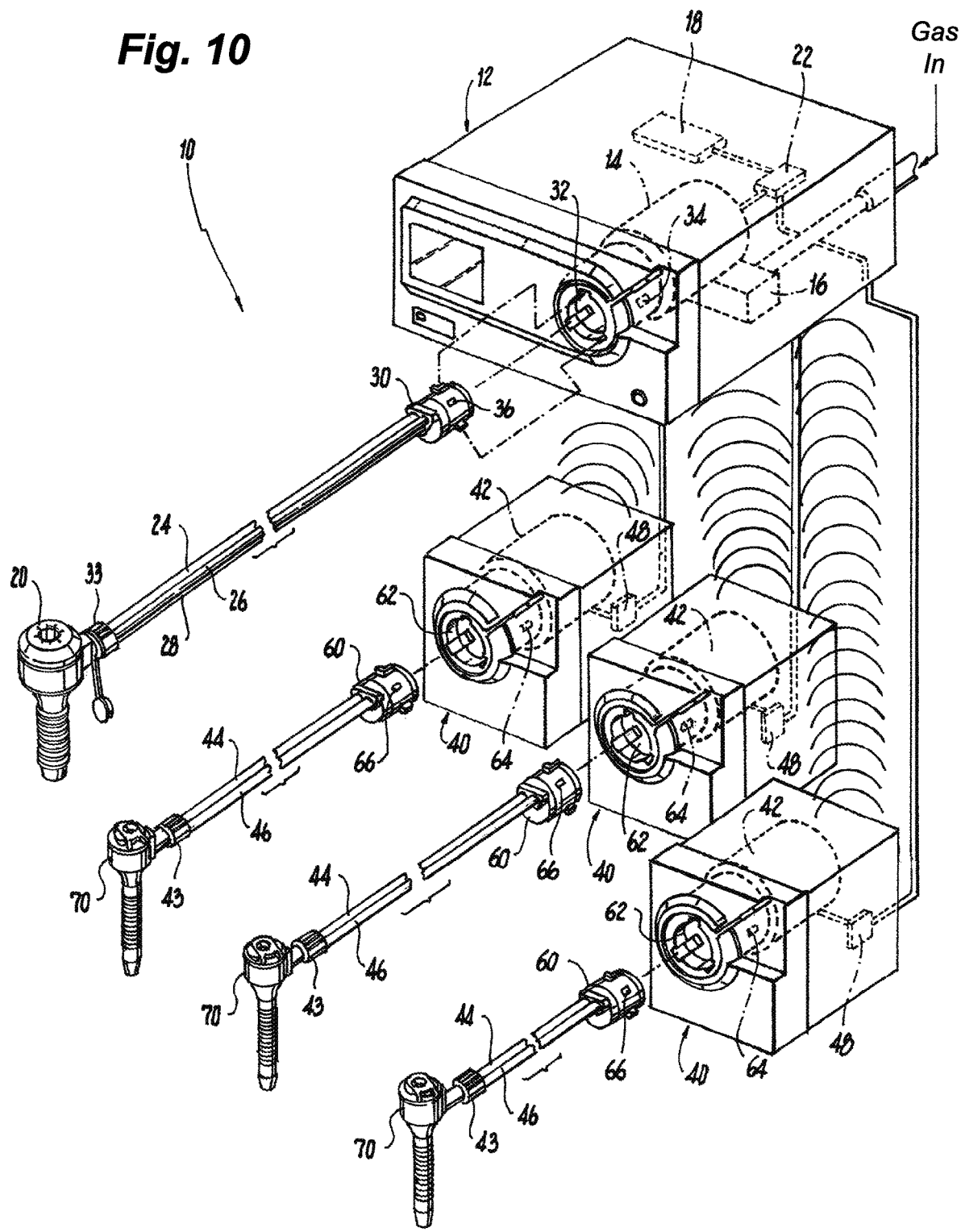
FIG. 10 is a perspective view of another embodiment of the networked gas circulation system of the subject invention, wherein a dual lumen gas sealed access port is associated with the primary gas circulation device and a single lumen gas sealed access port is associated with each secondary gas circulation device in the network.

Referring now to FIG. 10, there is illustrated another embodiment of the gas circulation system 10 of the subject invention, which includes a primary gas circulation device 12 and a plurality of networked subordinate gas circulation devices 40, in the same configuration as depicted in FIGS. 1 and 5 above. In this embodiment however, the access devices differ somewhat from those illustrated in FIGS. 1 and 5. In particular, the primary gas circulation device 12 is in pneumatic communication with a dual lumen gas sealed access port 20 (see FIG. 2; and U.S. Pat. No. 8,795,223) and each of the subordinate gas circulation devices 40 are in pneumatic communication with a single lumen gas sealed access port 70 (see FIGS. 5 and 6; and U.S. Patent Application Publication No. 2018/0256205).

Figure 11:
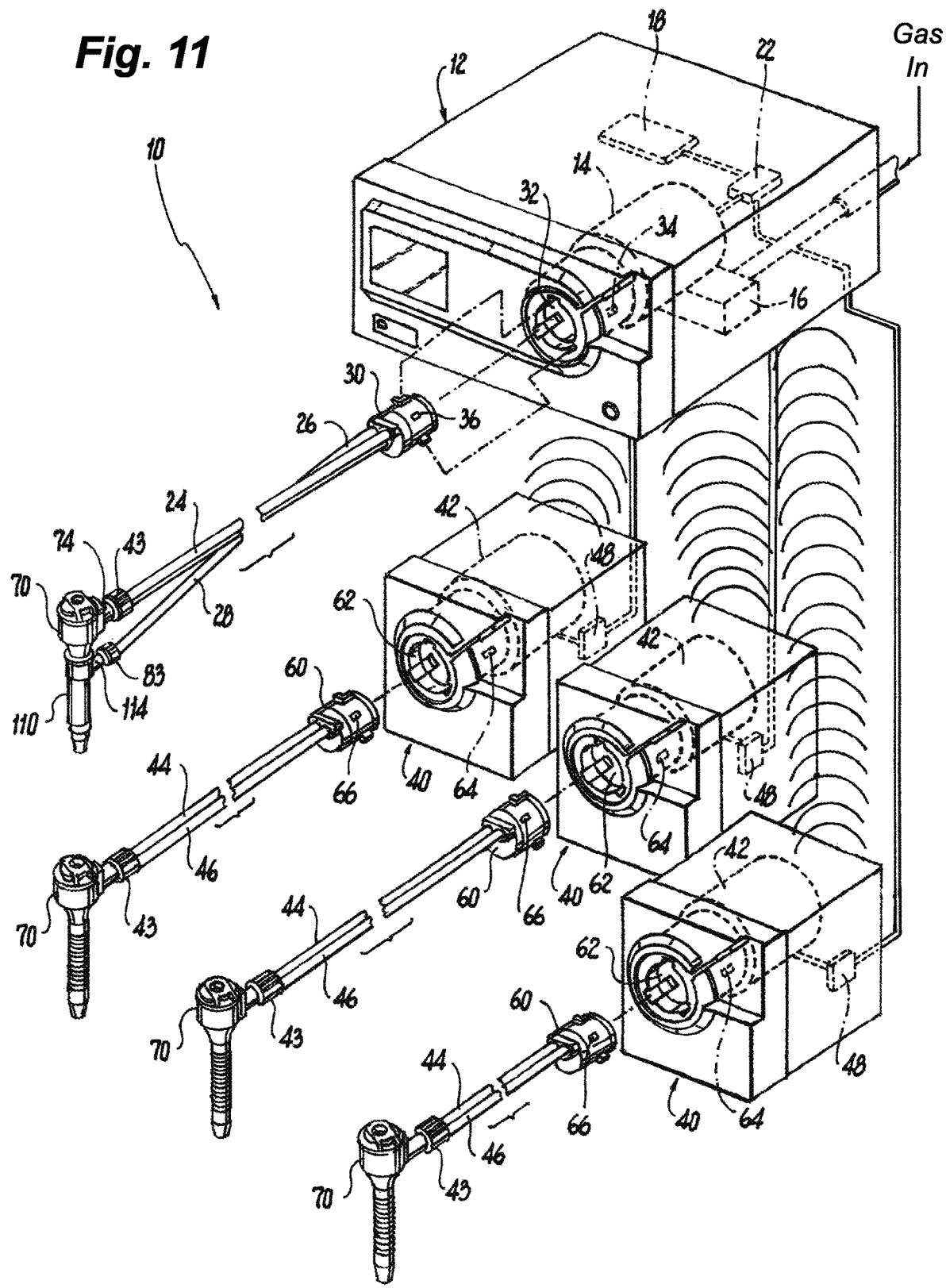
FIG. 11 is a perspective view of yet another embodiment of the networked gas circulation system of the subject invention, wherein a single lumen gas sealed access port disposed within an insufflation and sensing sleeve is associated with the primary gas circulation device and a single lumen gas sealed access port is associated with each secondary gas circulation device in the network.
Figure 12:
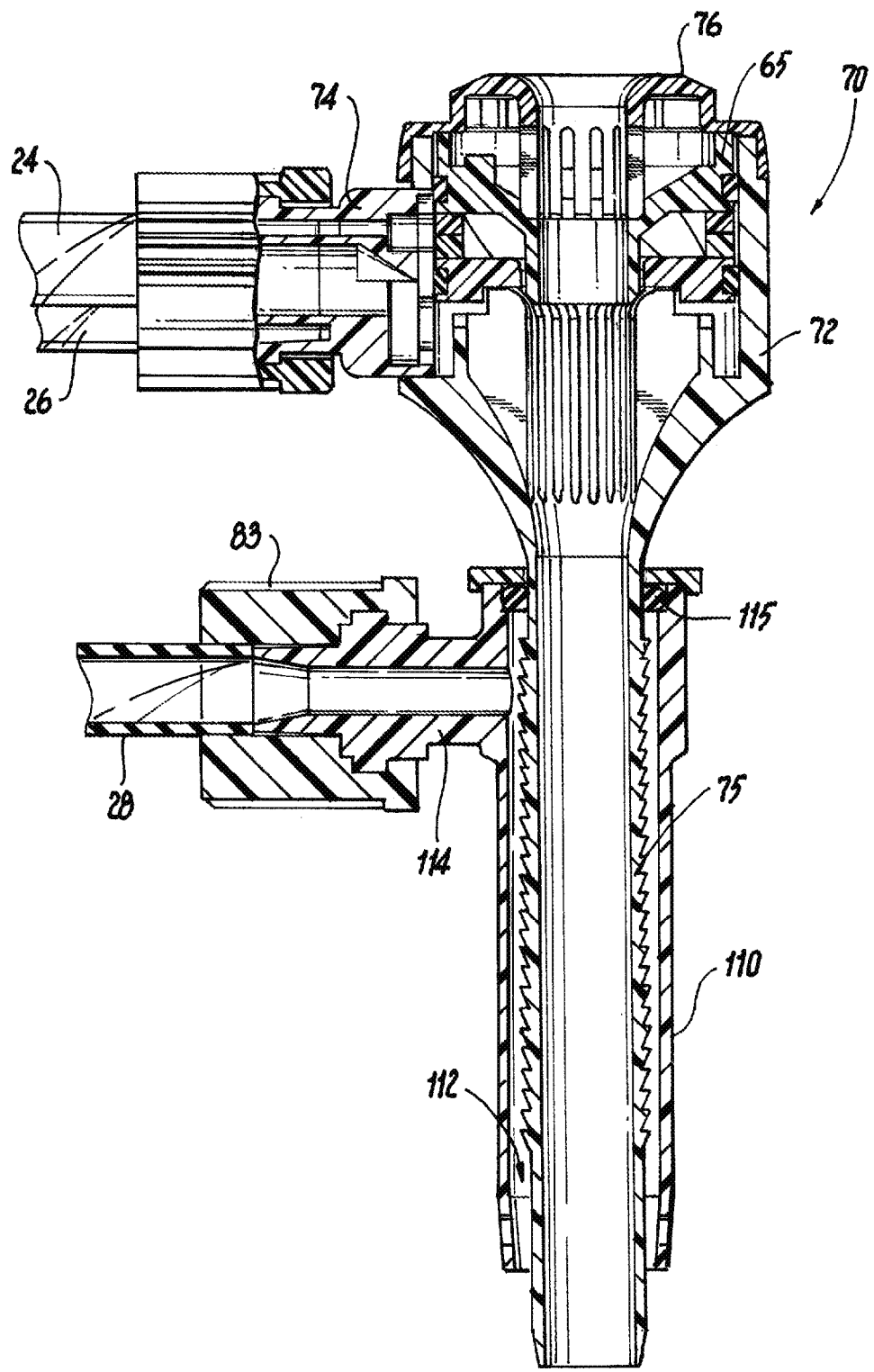
FIG. 12 is an enlarged cross-sectional view of the single lumen gas sealed access port of FIG. 9 disposed within an insufflation and sensing sleeve as shown in FIG. 11.

Referring now to FIG. 11, there is illustrated yet another embodiment of the gas circulation system 10 of the subject invention, which includes a primary gas circulation device 12 and a plurality of networked subordinate gas circulation devices 40, in the same configuration as depicted in FIG. 1 above. In this embodiment however, the access devices differ from those previously described and illustrated. In particular, the primary gas circulation device 12 is in pneumatic communication with a single lumen gas sealed access port 70 of the type shown in FIGS. 5 and 6 that is coaxially installed within an insufflation sleeve 110 as shown in FIG. 12 and described in detail below. This configuration is functionally similar to the dual lumen gas sealed access port 20 shown in FIG. 2.

Referring to FIG. 12, the primary gas delivery device 12 communicates with a single lumen gas sealed access port 70 that is coaxially installed within an insufflation sleeve 110. The access port 70 communicates with the gas delivery device 12 by way of a gas delivery lumen 24 and a gas return lumen 26, and the insufflation sleeve 110 communicates with the gas delivery device 12 by way of an insufflation lumen 28. More particularly, the sleeve 110 has a single lumen connector 114 that cooperates with a coupling 83 on the distal end of insufflation lumen 28. A seal 115 is provided within the interior bore 112 of insufflation sleeve 110 to form an annular insufflation and sensing channel around the tubular body 75 of coaxially installed access port 70. A multi-lumen tube set for use with the system of FIGS. 11 and 12 is disclosed in U.S. Patent Application Publication No. 2018/0256204, which has been previously incorporated by reference.

Figure 13:
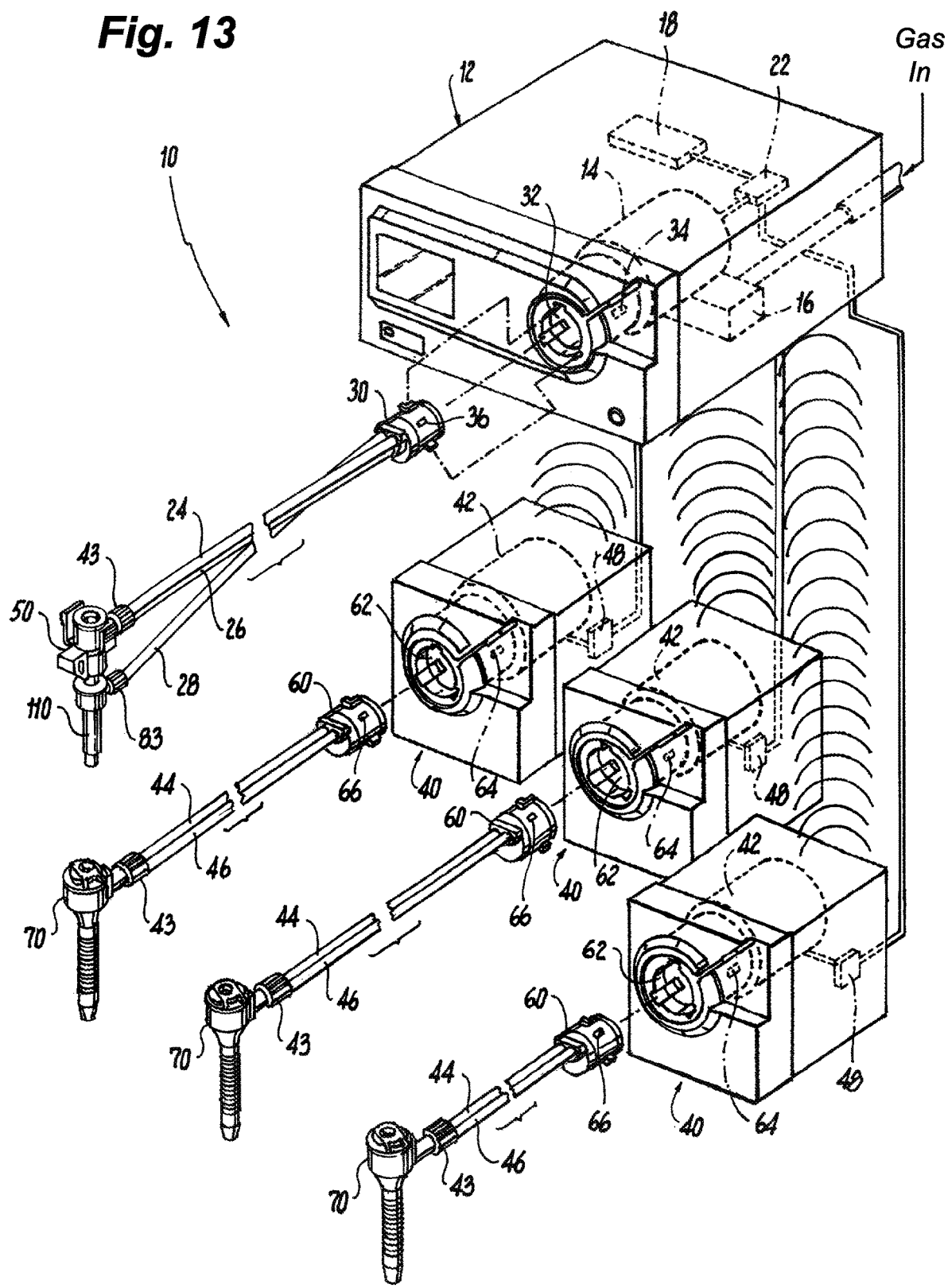
FIG. 13 is a perspective view of still another embodiment of the networked gas circulation system of the subject invention, wherein a two-part single lumen gas sealed access port disposed within an insufflation and sensing sleeve is associated with the primary gas circulation device and a single lumen gas sealed access port is associated with each secondary gas circulation device in the network.
Figure 14:
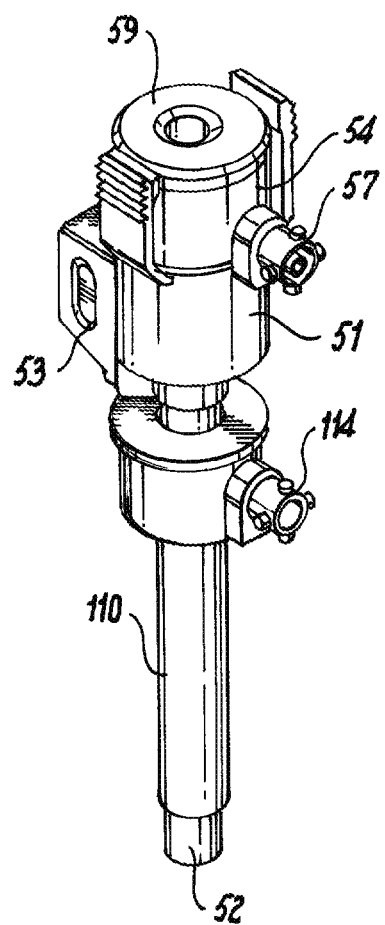
FIG. 14 is an enlarged perspective view of the two-part single lumen gas sealed access port disposed within an insufflation and sensing sleeve as shown in FIG. 13.

Referring now to FIG. 13, there is illustrated still another embodiment of the gas circulation system 10 of the subject invention, which includes a primary gas circulation device 12 and a plurality of networked subordinate gas circulation devices 40, in the same configuration as depicted in FIG. 1 above. In this embodiment however, the access devices differ somewhat from those previously described and illustrated in FIG. 11. In particular, the primary gas circulation device 12 is in pneumatic communication with a two-part single lumen gas sealed access port 50 (see FIGS. 3 and 4) that is coaxially installed within an insufflation sleeve 110, as shown in FIG. 14.

More particularly, the two-part access port 50 communicates with the gas delivery device 12 by way of a gas delivery lumen 24 and a gas return lumen 26, and the insufflation sleeve 110 communicates with the gas delivery device 12 by way of an insufflation lumen 28. A multi-lumen tube set for use with the system of FIGS. 13 and 14 is disclosed in U.S. Patent Application Publication No. 2018/0256204, which has been previously incorporated by reference.

Figure 15:
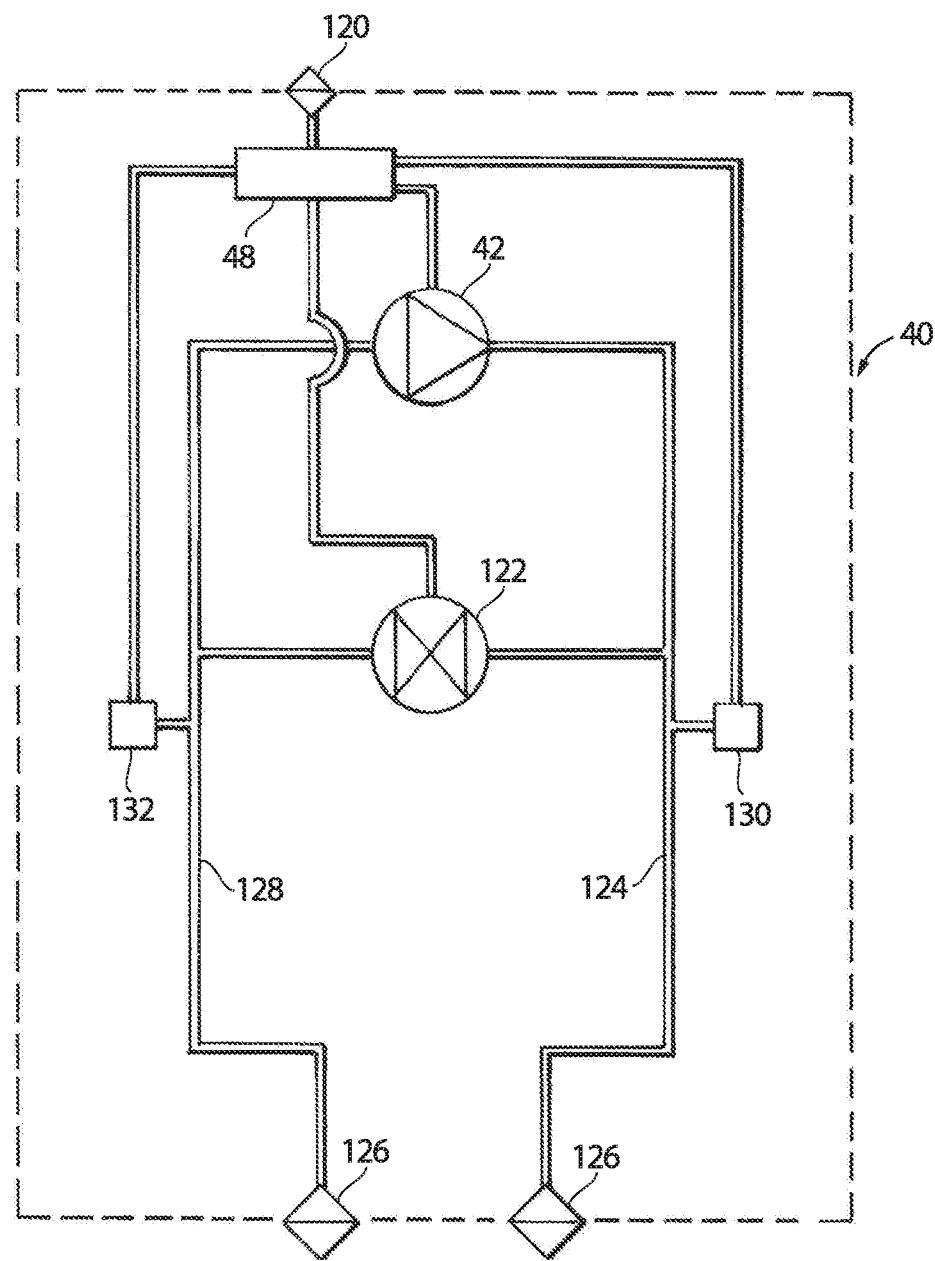
FIG. 15 is a schematic representation of the secondary gas circulation device of the subject invention, configured with an AC motor for driving the pump associated with a gas sealed trocar.

Referring now to FIG. 15, there is illustrated is a schematic representation of the subordinate gas circulation device 40 of the subject invention, which includes the AC pump 42 for gas circulation and the subordinate pump controller 48. The subordinate pump controller 48 communicates with the CPU 18 of the primary gas delivery device 12 through wired or wireless communication means by way of an input coupling 120 to modify the behavior of the pump 42. In addition, the subordinate gas circulation device 40 includes a by-pass valve 122 connected to the subordinate pump controller 48 to adjust the flow rate of the pump output.

A gas delivery line 124 extends from the output side of pump 42 to a filter interface 126 (located within the portal 62 of each device 40 shown in FIG. 1), and a gas return line 128 extends from the filter interface 126 to the input side of the pump 42. A positive pressure sensor 130 is operatively associated with the gas delivery line 124 and a negative pressure sensor 132 is operatively associated with the gas return line 128. The pressure sensors 130 and 132 provide pressure based control signals to the pump controller 48 for modifying the behavior of the pump 42.

Figure 16:
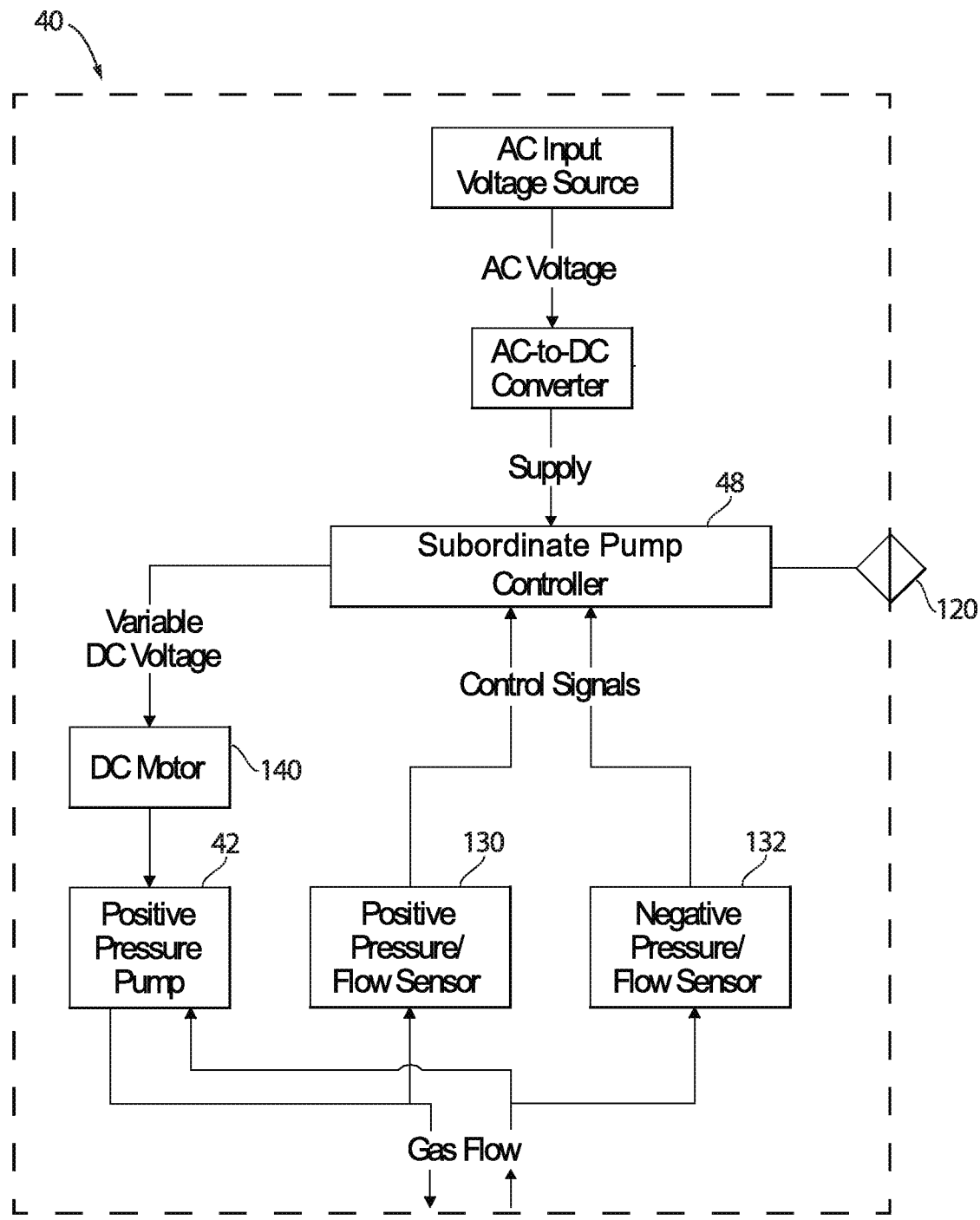
FIG. 16 is a schematic representation of the secondary gas circulation device of the subject invention, configured with a DC motor for driving the pump associated with a gas sealed trocar.

Alternatively, as illustrated in FIG. 16, the subordinate gas circulation device 40 of the subject invention could be configured with a DC motor 140 for driving the positive pressure gas circulation pump 42 as commanded by the subordinate pump controller 48 through control signals received from a positive pressure sensor 130 and a negative pressure sensor 132. The subordinate pump controller 48 communicates with the CPU 18 of the primary gas delivery device 12 through wired or wireless communication means by way of an input coupling 120 to modify the behavior of the pump 42.

Those skilled in the art will readily appreciate that the primary gas delivery device 12 and each subordinate gas delivery device 40 will be connected to a power source. In this regard, power may be routed to the subordinate devices 40 by way of the primary device 12, or each subordinate device 40 may be directly connected to a power source.

While the subject invention has been shown and described with reference to various embodiments, those skilled in the art will readily appreciate that changes and/or modifications may be made thereto without departing from the scope of the subject disclosure. For example, those skilled in the art will readily appreciate that the primary and the secondary access devices described and illustrated throughout the specification, could be readily interchanged with one another and utilized in any combination, without limitation.

What is claimed is:

1. A system for performing an endoscopic surgical procedure in a surgical cavity, comprising:
   a) a primary gas circulation device housing a primary pump configured to deliver a flow of pressurized gas to a primary gas delivery lumen and to receive gas from a primary gas return lumen;
   b) a primary gas sealed access port configured to receive pressurized gas from the primary gas delivery lumen to generate a gaseous seal therein and to return gas used to generate the gaseous seal back to the primary pump through the primary gas return lumen, so as to maintain a stable pressure level within the surgical cavity, wherein the primary gas sealed access port is a dual lumen gas sealed access port that includes coaxially arranged inner and outer tubular body portions defining an annular insufflation passage therebetween to accommodate delivery of insufflation gas into the surgical cavity, and wherein the inner tubular body portion is configured to accommodate gas sealed passage of a surgical instrument into the surgical cavity;

c) at least one subordinate gas circulation device, separate from, in communication with and controlled by the primary gas circulation device and housing a subordinate pump configured to deliver a flow of pressurized gas to a subordinate gas delivery lumen and to receive gas from a subordinate gas return lumen; and d) at least one subordinate gas sealed access port configured to receive pressurized gas from the subordinate gas delivery lumen to generate a gaseous seal therein and to return gas used to generate the gaseous seal back to the subordinate pump through a subordinate gas return lumen, wherein the at least one subordinate gas sealed access port is a single lumen gas sealed access port that includes a single tubular body portion configured to accommodate gas sealed passage of another surgical instrument into the surgical cavity, and wherein the subordinate pump housed in the at least one subordinate gas circulation device is configured to provide only enough output power to generate the gaseous seal in the single lumen gas sealed access port.

2. A system as recited in claim 1, wherein the primary gas circulation device further houses an insufflator for delivering insufflation gas to the surgical cavity through the insufflation passage and periodically measuring pressure within the surgical cavity through the insufflation passage.

3. A system as recited in claim 2, further comprising a primary filter cartridge configured for reception in the primary gas circulation device to communicate with the primary gas delivery lumen, the primary gas return lumen and the insufflation lumen.

4. A system as recited in claim 1, further comprising a primary filter cartridge configured for reception in the primary gas circulation device to communicate with the primary gas delivery lumen and the primary gas return lumen.

5. A system as recited in claim 1, wherein the at least one subordinate gas circulation device includes a subordinate filter cartridge communicating with the subordinate gas delivery lumen and the subordinate gas return lumen.

6. A system as recited in claim 1, wherein the primary gas circulation device includes a data reader for detecting a machine readable data signature of a primary filter cartridge received therein to determine a physical characteristic of the cartridge and/or number of lumens associated therewith.

7. A system as recited in claim 1, wherein the at least one subordinate gas circulation device includes a data reader for detecting a machine readable data signature of a subordinate filter cartridge received therein to determine a physical characteristic of the cartridge and/or number of lumens associated therewith.

8. A system as recited in claim 1, wherein the primary gas circulation device houses a central processor for controlling the primary pump of the primary gas circulation device and the subordinate pump of the at least one subordinate gas circulation device.

9. A system as recited in claim 8, wherein the subordinate pump of the at least subordinate gas circulation device is driven by AC power.

10. A system as recited in claim 8, wherein the subordinate pump of the at least subordinate gas circulation device is driven by a DC motor.

11. A system as recited in claim 8, wherein the at least one subordinate gas circulation device is in wireless communication with the central processor of the primary gas circulation device.

12. A system as recited in claim 8, wherein the at least one subordinate gas circulation device is in wired communication with the central processor of the primary gas circulation device.

13. A system as recited in claim 8, wherein a plurality of subordinate gas circulation devices are in networked communication with and controlled by the central processor of the primary gas circulation device.

14. A system as recited in claim 13, wherein each of the plurality of subordinate gas circulation devices is configured to deliver a flow of pressurized gas to a respective subordinate gas delivery lumen connected to a respective subordinate gas sealed access port and to receive gas from a respective subordinate gas return lumen connected to the respective subordinate gas sealed access port.

15. A system as recited in claim 8, wherein the central processor of the primary gas circulation device is adapted and configured to conduct a multi-staged calibration process for calibrating a pneumatic performance range of the primary gas sealed access port and the at least one subordinate gas sealed access port.

16. A system as recited in claim 1, wherein only the primary pump is configured to provide sufficient output power to compensate for leakage from the surgical cavity.

17. A system for performing an endoscopic surgical procedure in a surgical cavity, comprising:
a) a primary gas circulation device housing a central processor and a primary pump, the primary pump controlled by the central processor and configured to deliver a flow of pressurized gas to a primary gas delivery lumen and to receive gas from a primary gas return lumen; and
b) a plurality of separate subordinate gas circulation devices each housing a respective subordinate pump configured to deliver a flow of pressurized gas to a respective subordinate gas delivery lumen and to receive gas from a respective subordinate gas return lumen, wherein the subordinate pump in each subordinate gas circulation device is in networked communication with and controlled by the central processor of the primary gas circulation device, and wherein only the primary pump is configured to provide sufficient output power to compensate for leakage from the surgical cavity.

18. A system as recited in claim 17, wherein the primary gas circulation device also houses an insufflator configured to deliver insufflation gas to the surgical cavity through an insufflation lumen and for periodically measuring pressure within the surgical cavity through the insufflation lumen.

19. A system as recited in claim 18, further comprising a primary gas sealed access port configured to receive pressurized gas from the primary gas delivery lumen to generate a gaseous seal therein and to return gas used to generate the gaseous seal back to the primary pump through the primary gas return lumen, so as to maintain a stable pressure level within the surgical cavity.

20. A system as recited in claim 18, wherein the primary gas sealed access port is configured to receive insufflation gas from the insufflation lumen.

21. A system as recited in claim 20, wherein the primary gas sealed access port is a dual lumen gas sealed access port that includes coaxially arranged inner and outer tubular body portions defining an annular insufflation passage therebetween to accommodate delivery of insufflation gas into the surgical cavity, and wherein the inner tubular body portion is configured to accommodate gas sealed passage of a surgical instrument into the surgical cavity.

22. A system as recited in claim 18, further comprising a secondary gas sealed access port operatively associated with each subordinate gas circulation device and configured to receive pressurized gas from a respective subordinate gas delivery lumen to generate a gaseous seal therein and to return gas used to generate the gaseous seal back to a respective subordinate pump through a respective subordinate gas return lumen.

23. A system as recited in claim 22, wherein each secondary gas sealed access port is a single lumen gas sealed access port that includes a single tubular body portion configured to accommodate gas sealed passage of another surgical instrument into the surgical cavity.

24. A system as recited in claim 23, wherein each subordinate pump is configured to provide only enough output power to generate the gaseous seal in the secondary gas sealed access port associated therewith.

25. A system as recited in claim 17, wherein the primary gas circulation device is responsible for smoke evacuation from the surgical cavity and for handling over-pressure conditions in which gas is released from the surgical cavity and under-pressure conditions in which air is entrained into the surgical cavity.

* * * * *